US007812145B2

(12) United States Patent
Hsu et al.

(10) Patent No.: US 7,812,145 B2
(45) Date of Patent: Oct. 12, 2010

(54) SHORT ISOFORM OF ANNEXIN A10 AT CHROMOSOME 4Q, TERMED ANNEXIN 10S (ANXA 10S) AND METHODS OF USE

(75) Inventors: Hey-Chi Hsu, Kaohsiung (TW); David C. P. Chen, Kaohsiung (TW)

(73) Assignee: Asia Hepato Gene Company, Kaohsiung (TW)

( * ) Notice: Subject to any disclaimer, the term of this patent is extended or adjusted under 35 U.S.C. 154(b) by 0 days.

(21) Appl. No.: 12/346,241

(22) Filed: Dec. 30, 2008

(65) Prior Publication Data
US 2009/0227015 A1 Sep. 10, 2009

Related U.S. Application Data

(62) Division of application No. 11/088,331, filed on Mar. 24, 2005, now Pat. No. 7,495,073.

(51) Int. Cl.
C07H 21/04 (2006.01)
C12N 15/00 (2006.01)
C12N 5/10 (2006.01)
(52) U.S. Cl. ............ 536/23.5; 435/320.1; 435/325
(58) Field of Classification Search ............ None
See application file for complete search history.

(56) References Cited

U.S. PATENT DOCUMENTS 6,653,445 B1 * 11/2003 Ni et al. ............ 530/350

OTHER PUBLICATIONS

NCBI, GenBank AY626137, Peng et al, published Jun. 12, 2004, 4 pages.*
Ausubel et al (Current Protocols in molecular Biology, 1995, 3rd edition, Wiley & Sons, NY, Section 9, p. 9-1 to 9-14).*
Bando K, Nagai H, Matsumoto S, Koyama M, Kawamura N, Onda M, Emi M: Identification of a 1-cM region of common deletion on 4q35 associated with progression of hepatocellular carcinoma. *Genes Chromosomes Cancer* 1999, 25:284-289.
Behrend E I, Craig A M, Wioson S M, Denhardt D T, Chambers A F. Reduced malignancy of ras-transformed NIH 3T3 cells expressing antisense osteopontin RNA. *Cancer Res* 1994;54:832-837.
Chou Y H, Chung K C, Jeng L B, Chen T C, Liaw Y F. Frequent allelic loss on chromosomes 4q and 16q associated with human hepatocellular carcinoma in Taiwan. *Cancer Lett* 1998; 123:1-6.
Deloukas P, et al. (>40 authors). A physical map of 30,000 human genes. *Science* 1998, 282:744-746.
El-Tanani M, Barraclough R, Wilkinson M C, Rudland P S. Metastasis-inducing dna regulates the expression of the osteopontin gene by binding the transcription factor tcf-4. *Cancer Res* 2001;61:5619-5629.
GenBank, Accession No. AAT42216, Jun. 12, 2004, Peng et al, p. 1-2.
Gotoh M, Sakamoto M, Kanetaka K, Chuuma M, Hirohashi S. Overexpression of osteopontin in hepatocellular carcinoma. *Pathol Int* 2002;52:19-24.

Guan X Y, Fang Y, Sham J S, Kwong D L, Zhang Y, Liang Q, Li H, Zhou H, Trent J M. Recurrent chromosome alterations in hepatocellular carcinoma detected by comparative genomic hybridization. *Genes Chromosomes Cancer* 2000;29:110-116.
Hsu H C, Chiou T J, Chen Z Y, Lee C S, Lee P H, Peng S Y. Clonality and clonal evolution of hepatocellular carcinoma with multiple nodules. *Hepatology* 1991;13:923-928.
Hsu H C, Jeng Y M, Mao T L, Chu J S, Lai P L, Peng S Y. β-Catenin mutations are associated with a subset of low stage hepatocellular carcinoma negative for hepatitis B virus and with favorable prognosis. *Am J Pathol* 2000;157:763-770.
Hsu H C, Wu T T, Wu M Z, Sheu J C, Lee C S, Chen D S. Tumor Invasiveness and prognosis in resected hepatocellular carcinoma: Clinical and pathogenetic implications. *Cancer* 1988;61:2095-2099.
Imamura H, Matsuyama Y, Tanaka E, Ohkubo T, Hasegawa K, Miyagawa S, Sugawara Y, Minagawa M, Takayama T, Kawasaki S, Makuuchi M. Risk factors contributing to early and late phase intrahepatic recurrence of hepatocellular carcinoma after hepatectomy. *J Hepatol* 2003;38:200-207.
Kusano N, Shiraishi K, Kubo K, Oga A, Okita K, Sasaki K. Genetic aberrations detected by comparative genomic hybridization in hepatocellular carcinomas: their relationship to clinicopathological features. *Hepatology* 1999;29:1858-1862.
Li M S, Li P F, He S P, Du G G, Li G. The promoting molecular mechanism of alpha-fetoprotein on the growth of human hepatoma. Bel7402 cell line. *World J Gastroenterol* 2002;8:469-475.
Li M S, Li P F, Yang F Y, He S P, Du G G, Li G. The intracellular mechanism of alpha-fetoprotein promoting the proliferation of NIH 3T3 cells. *Cell Res* 2002;12:151-156.
Li Y, Tang Z Y, Ye S L, Liu Y K, Chen J, Xue Q, Chen J, Gao D M, Bao W H. Establishment of cell clones with different metastatic potential from the metastatic hepatocellular carcinoma cell line MHCC97. *World J Gastroenterol* 2001;7:630-636.
Liu S H, Lin C Y, Peng S Y, Jeng Y M, Pan H W, Cheng W, Kuo M Y P, Hsu H C. Down-regulation of Annexin A10 in hepatocellular carcinoma is associated with vascular invasion, early recurrence, and poor prognosis in synergy with p53 mutation. *Am J Pathol* 2002; 160:1831-1837.

(Continued)

*Primary Examiner*—Laura B Goddard
(74) *Attorney, Agent, or Firm*—Occhiuti Rohlicek & Tsao LLP

(57) ABSTRACT

The present invention includes compositions including a novel short isoform of Annexin A10, termed Annexin 10s (ANXA10s) and methods of use. The compositions include nucleic acid molecules encoding ANXA10s, ANXA10s polypeptides, ANXA10s amino acid sequences and derivatives or modifications thereof. Included in these methods are the interrelation of the aberrant expressions of AFP, OPN, and the novel liver specific short isoform, ANXA10s, at human Chromosome 4q in the progression of hepatocellular carcinoma (HCC). The aberrant expressions of AFP, OPN and ANXA10s are shown to act cooperatively toward advanced disease, which could be useful for diagnostic, molecular staging or treatment of a patient having HCC or at risk of developing HCC.

6 Claims, 4 Drawing Sheets

OTHER PUBLICATIONS

Ma X J, Salunga R, Tuggle J T, Gaudet J, Enright E, McQuary P, Payette T, Pistone M, Stecker K, Zhang B M, Zhou Y X, Varnholt H, Smith B, Gadd M, Chatfield E, Kessler J, Baer T M, Erlander M G, Sgroi D C. Gene expression profiles of human breast cancer progression. *Proc Natl Acad Sci U S A*. 2003;100:5974-5799.

Marchio A, Meddeb M, Pineau P, Danglot G, Tiollais P, Bernheim A, Dejean A. Recurrent chromosomal abnormalities in hepatocellular carcinoma detected by comparative genomic hybridization. *Genes Chromosomes Cancer* 1997;18:59-65.

McGowan-Jordan I J, Speevak M D, Blakey D, Cevrette M: Suppression of tumorigenicity in human teratocarcinoma cell line PA-1 by introduction of chromosome 4. *Cancer Res* 1994, 54:2568-2572.

Medico E, Gentile A, Lo Celso C, Williams T A, Gambarotta G, Trusolino L, Comoglio P M. Osteopontin is an autocrine mediator of hepatocyte growth factor-induced invasive growth. *Cancer Res* 2001;61:5861-5868.

Morgan R O, Fernandez M P: Annexin gene structures and molecular evolutionary genetics. *Cell Mol Life Sci* 1997, 53: 508-515.

Morgan R O, Jenkins N A, Gilbert D J, Copeland N G, Balsara B R, Testa J R, Fernandez M P. Novel human and mouse annexin A10 are linked to the genome duplications during early chordate evolution. *Genomics* 1999;60:40-49.

Moss S E, Morgan R O. The annexins. *Genome Biol* 2004;5:219.1-219.8.

NCBI "Sequence Revision History", 1 page.

Nomura F, Ohnishi K, Tanabe Y. Clinical features and prognosis of hepatocellular carcinoma with reference to serum alpha-fetoprotein levels: analysis of 606 patients. *Cancer* 1989;64:1700-1707.

Pan H W, Ou Y H, Peng S Y, Liu S H, Lai P L, Lee P H, Sheu J C, Chen C L, Hsu H C. Overexpression of osteopontin is associated with intrahepatic metastasis, early recurrence, and poorer prognosis of surgically resected hepatocellular carcinoma. *Cancer* 2003; 98:119-127.

Peng S Y, Chen W J, Lai P L, Jeng Y M, Sheu J C, Hsu H C. High α-fetoprotein level with high stage, early recurrence and poor prognosis of hepatocellular carcinoma: Significance of hepatitis B virus infection, age, p53 and .beta.-catenin mutations. *Int J Cancer* 2004; vol. 112 (in press).

Piao Z, Park C, Park J H, Kim H. Deletion mapping of chromosome 4q in hepatocellular carcinoma. *Int J Cancer* 1998;79:356-360.

Tuck A B, Arsenault D M, O'Malley F P, Hota C, Ling M C, Wilson S M, Chambers A F. Osteopontin induces increased invasiveness and plasminogen activator expression of human mammary epithelial cells. *Oncogene* 1999;18:4237-4246.

van't Veer L J, Dai -H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer. *Nature* 2002;415:530-536.

Wang X W, Xu B. Stimulation of tumor-cell growth by alpha-fetoprotein. *Int J Cancer* 1998; 75:596-599.

Wong N, Lai P, Lee S W, Fan S, Pang E, Liew C T, Sheng Z, Lau J W, Johnson P J. Assessment of genetic changes in hepatocellular carcinoma by comparative genomic hybridization analysis: relationship to disease stage, tumor size, and cirrhosis. *Am J Pathol* 1999;154:37-43.

Wong N, Lai P, Pang E, Fung L F, Sheng Z, Wong V, Wang W, Hayashi Y, Perlman E, Yuna S, Lau J W, Johnson P J. Genomic aberrations in human hepatocellular carcinomas of differing etiologies. *Clin Cancer Res* 2000;6:4000-4009.

Ye Q H, Qin L X, Forgues M, He P, Kim J W, Peng A C, Simon R, Li Y, Robles A I, Chen Y, Ma Z C, Wu Z Q, Ye S L, Liu Y K, Tang Z Y, Wang X W. Predicting hepatitis B virus-positive metastatic hepatocellular carcinomas using gene expression profiling and supervised machine learning. *Nat Med* 2003;9:416-423.

Zondervan P E, Wink J, Alers J C, IJzermans J N, Schalm S W, de Man R A, van Dekken H. Molecular cytogenetic evaluation of virus-associated and non-viral hepatocellular carcinoma: analysis of 26 carcinomas and 12 concurrent dysplasias. *J. Pathol* 2000;192:207-215.

* cited by examiner

SHORT ISOFORM OF ANNEXIN A10 AT CHROMOSOME 4Q, TERMED ANNEXIN 10S (ANXA 10S) AND METHODS OF USE

This application is a divisional of U.S. Ser. No. 11/088,331, filed on Mar. 24, 2005, now U.S. Pat. No. 7,495,073, the content of which is hereby incorporated by reference in its entirety.

STATEMENT REGARDING FEDERALLY SPONSORED RESEARCH AND DEVELOPMENT

This invention was made with government support awarded by the National Health Research Institute, Department of Health of the Republic of China, Taiwan (NHRI-GT-EX89B701L to HCH); the National Science Council of the Republic of China (NSC90-2314-B-227-001 to SYP, and NSC92-2314-B002-019 to HCH); and the Ministry of Economic Affairs (92-EC-17-A-17-i5-0005 to DCPC). The Republic of China may have certain rights in the invention.

TECHNICAL FIELD

The present application relates to compositions and methods with diagnostic or therapeutic utility for hepatocellular carcinoma. More specifically the present invention provides a compositions including a novel short isoform of Annexin A1O, termed Annexin 1Os (ANXA1Os), having decreased presence or expression in a hepatocellular carcinoma sample than a normal liver tissue sample and methods of using ANXA1Os in 20 the detection, staging or treatment of hepatocellular carcinoma

BACKGROUND OF THE INVENTION

Chromosome 4q includes one of the most frequent chromosomal regions exhibiting high frequency of allelic losses in hepatocellular carcinoma (HCC),[1-5] with commonly deleted regions at 4q21-22, 4q26-q27, and 4q35.[6,7] Chromosomal alterations at 4q are of great interest because it is a unique trait for HCC,[8] and 4q contains genes expressed predominantly in the liver. Introduction of human chromosome 4 suppressed the tumorigenicity of teratocarcinoma cell PA-1 in nude mice.[9] Studies have shown that 4q alterations are more frequently associated with advanced stage and poor differentiation.[3,7,10,11] These findings indicate the existence of tumor suppressor gene(s) at this region. But, it was also shown that the loss of 4q in HCC did not correlate with tumor differentiation and vascular invasion,[12] and the frequent loss of 4q was observed in the preneoplastic liver cell dysplasia.[13] The reasons for these discrepancies remain to be elucidated.

BRIEF SUMMARY OF THE INVENTION

The present invention includes an isolated or recombinant nucleic acid molecule consisting essentially of a nucleic acid sequence according to SEQ ID NO: 1, a nucleic acid sequence encoding the amino acid sequence according to SEQ ID NO: 2, or a nucleic acid sequence encoding the amino acid sequence of an annexin 1Os (ANXAIOs) polypeptide. The nucleic acid sequence may be a cDNA, isolated genomic DNA, 10 synthetic DNA, isolated mRNA and the like. The abundance of ANXAI Os mRNA was found significantly lower in a hepatocellular carcinoma sample than a normal liver sample.

The present invention also includes a polypeptide consisting essentially of the amino acid sequence of SEQ ill NO: 2 or an amino acid sequence encoding a ANXA1Os 15 polypeptide. The polypeptide may be expressed lower in a heptocellular carcinoma sample than a normal sample.

The present invention also includes an expression vector and a transfected or transformed host cell utilizing the nucleic acid sequence of SEQ ID NO: 1 or a nucleic acid sequence encoding a ANXA1Os amino acid sequence and a polyclonal antibody or antibody fragment able to bind the ANXAI0s polypeptide.

The present invention also includes a method of diagnosing a patient with or at risk of developing hepatocellular carcinoma including obtaining a biological sample from an individual suspected of having heptocellular carcinoma (HCC) or at risk of developing HCC, measuring the amount of ANXA1Os in the biological sample, comparing the measured amount of ANXAIOs to a control, and determining the patient has or is at risk of developing hepatocellular carcinoma if the amount of ANXA1Os is less in the patient sample than the control. The method may also include measuring the amount of osteopontin (OPN) and alpha-fetoprotein (AFP) in the sample and comparing the measurements to a control value or control sample. A decreased amount or expression of ANXAI0s and an increased amount or expression of osteopontin (OPN) and alpha-fetoprotein (AFP) is indicative of increased risk of having or developing hepatocellular carcinoma.

The present invention also includes a method of staging the progression of hepatocelluar carcinoma including obtaining a biological sample from an individual suspected of having hepatocellular carcinoma or at risk of developing hepatocellular carcinoma, measuring a level of gene expression of each of ANXA1Os, osteopontin, and alpha-fetoprotein in the biological sample, comparing the levels of gene expression to a corresponding control ANXA1Os value, a control osteopontin value or a control alphafetoprotein value, determining an expression profile indicative of the comparisons, and comparing the expression profile to a predetermined set of data corresponding to hepatocellular carcinoma tumor progression. Methods may include utilizing 5' and 3' primers for ANXA1Os, osteopontin and alpha-fetoprotein nucleic acid molecules.

BRIEF DESCRIPTION OF THE DRAWINGS

FIG. 2A shows that AFP mRNA was detected in 9 representative HCCs with serum AFP levels above 200 ng/ml and a HCC of 2 em with normal serum AFP level. FIG. 2B shows OPN mRNA was over expressed in 7 representative HCCs and in one liver. FIG. 2C shows that ANXA1Os 30 was detected in all the livers, but dramatically decreased in 8 HCCs. Controls PBGD and S26 designate porphobilinogen deaminase and S26 ribosomal protein mRNA, respectively.

DETAILED DESCRIPTION

Figure 1:
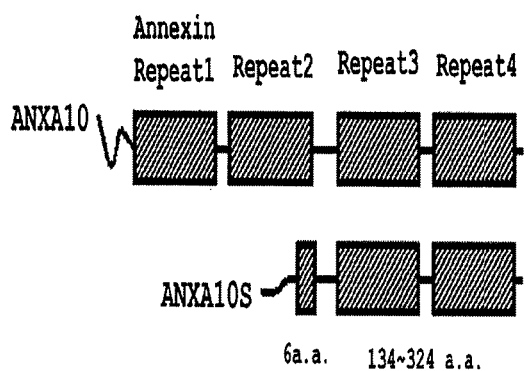
FIG. 1 shows a schematic drawing and the amino acid sequences of human annexin A10 (ANXA10) (SEQ ID NO: 17) and its nucleic acid sequence (SEQ ID NO:16), and the novel short human isoform of Annexin A10, termed Annexin 10s (ANXA10s) (SEQ ID NO 2) and its nucleic acid sequence (SEQ ID NO:15). ANXA10s lacks the 134 amino acids of N-terminus of ANXA10 and has a unique six amino acid residue portion derived from the intron 5 sequence at the amino-terminus and includes the 135th to 324th amino acids of ANXA10 (boxed). ANXA10s lacks the first and major part of the second repeat of ANXA10 that classically has four repeats in the core domain

The present invention includes compositions including a novel short isoform of Annexin A1O, termed Annexin 1Os (ANXA1Os) and methods of use. The compositions include nucleic acid molecules encoding ANXA1Os, ANXA1Os polypeptides, ANXA1Os amino acid sequences and derivatives or modifications thereof. Included in these 20 methods are the interrelation of the aberrant expressions of AFP, OPN, and the novel liver specific short isoform, ANXA1Os, at human Chromosome 4q in the progression of hepatocellular carcinoma (HCC). The aberrant expressions of AFP, OPN and ANXA1Os are shown to act cooperatively toward advanced disease, which could be useful for diagnostic, molecular staging or treatment of a patient having HCC or at risk of 25 developing HCC.

The relationship between annexin 1Os (ANXA1Os), osteopontin (OPN) and alphafetoprotein (AFP) were examined in relation to the diagnosing, staging and treatment of hepatocellular carcinoma (HCC). Biological samples were obtained from individuals having or at risk of developing hepatocellular carcinoma (HCC) and tested for the 30 presence or amount of ANXA1Os, osteopontin (OPN) and alphafetoprotein (AFP) transcript. Specifically, between 1987 and 1997, 909 surgically resected primary HCCs were pathologically assessed at the National Taiwan University Hospital. Of these, 294 included unifocal primary HCCs, as previously described,[18,26-30] with complete clinicopathological assesement.

The group of HCC patients included 231 males and 63 females. The HCC group had adequate liver function and received total surgical resection of the primary tumors, 29. None received transhepatic arterial embolization (TAE) or chemotherapy before surgery. The age of the patients ranged from 14 to 88 years with a mean average of about 55.9 years of age. Serum hepatitis B surface antigen (HBsAg) was detected in 203 cases, anti-HCV antibody in 94 cases, including 27 cases also positive for HBsAg, and 24 were 10 negative for both (8.2%).

The tissue samples were classified into four grades (I through IV) according to Example 1. Then mRNA was extracted from the tissue samples according to Example 2 and corresponding cDNA libraries were constructed from the polyadenylated mRNA. A control cDNA library was also constructed from polyadenylated mRNA from a normal liver tissue sample. Large scale quantitative analysis of AFP, OPN, ANXA 10, ANXA10s was performed using RT-PCR according to Example 3 with primers specific for AFP, OPN, ANXA 10 and ANXA10s.

Analysis of the study shows frequent over expression of AFP at 4q11-q13 (51%) and OPN at 4q21-q25 (53%), and the downregulation of a novel short isoform of annexin A10 (designated ANXA1Os) at 4q33 (67%) in the unifocal primary HCC group. The three aberrant expressions were all associated with more frequent high-grade (grade II to IV), and high-stage HCCs with portal vein invasion (stage IIIB and IV), and early tumor recurrence (all Ps<0.0001). All the odds ratios exceeded 1.0. In general, the magnitude of association was greatest for ANXA10s down regulation and equivalent for AFP overexpression and OPN overexpression. These findings indicate that the frequent aberrant expressions of the three genes located at 4q, a chromosome region exhibiting high frequency of allelic loss in HCC,[6,7] play important roles in the tumor progression of HCC. This suggestion accords with recent clinical and experimental observations that unravel the stimulatory activity of AFP on the proliferation of hepatoma cells,[19,21,33] and high AFP level contributes to greater metastatic potential of HCCs and early tumor recurrence.[31,34] Nude mice bearing tumor implants derived from HCC clones with high metastatic potential exhibited higher serum AFP level than those with low metastatic implants derived from the same parental cells.35 Clinical and experimental studies have also shown that OPN enhances invasive and metastatic potential of transformed cells and human cancers,36-40 Transfection of small DNA fragments obtained from human malignant breast cancer cell lines into a benign rat mammary cell line enhances OPN transcription and causes the cells to metastasize in syngeneic rats.[39] The frequent OPN overexpression in HCC is associated with more aggressive tumor,[14,24] tumor metastasis.f and poor prognosis." Taken together, these observations suggest that the overexpressions of AFP and OPN contribute to the metastatic potential and hence more frequent early recurrence of HCc.[25,31,39,40]

Annexin A1O (ANXA1O) was believed to be a novel member of the annexin family with unique loss of the calcium-binding site[41,42] and believed to be expressed in liver and often downregulated in HCC.[15] In this study, ANXA10 was expressed abundantly in the stomach, as described by Moss & and Morgan.f but not in the nontumor liver. In contrast the present invention discloses the nontumor liver expresses instead a novel shorter transcript of ANXA1O (designated ANXA1Os). ANXA1Os uses an alternative promoter in intron 5 of ANXA10, leading to a cDNA encoding a protein with truncation of the 134 amino acid residues at the amino-terminus and lacking the first and major part of the second repeat of the core domain, a structure fundamentally deviating from the annexin family that classically has 4 repeats.[41,42] Using primer sets specific for ANXA1O and ANXA10s, only ANXA10s was expressed constitutively in the adult liver, whereas ANXA10 expression was limited to a small number of HCCs and HCC cell lines. ANXA10s was often downregulated in HCC and the downregulation correlated with high tumor grade, portal vein invasion, and early tumor recurrence (all Ps<0.0000I), confirming our previous observation.f These findings demonstrate that ANXA1Os has potential tumor invasion and metastasis suppressor activity.

HCCs with AFP overexpression, OPN overexpression, or ANXA1Os downregulation are shown to exhibit about a two-fold increase in portal vein invasion than those without the change. Therefore these aberrant expressions may interact during the tumor progression. This is supported by findings that AFP overexpression closely correlated with OPN overexpression (P=0.0026) and ANXA1Os downregulation (P<0.00001), while OPN overexpression also closely correlated with ANXA1Os downregulation (P<0.00001). Any combination of two of these events (AFP overexpression and OPN overexpression, AFP overexpression and ANXA1Os downregulation, OPN overexpression and ANXA1Os downregulation) were associated with more frequent high tumor grade, high tumor stage with portal vein invasion (stages IIIB and IV), and early tumor recurrence (all Ps<0.0001). The magnitude of odds ratio for those with the presence of two genetic variants exceeded the projected sum of the solely presence of single variant. These pair-wise combination analyses revealed apparently interactive effects between these genetic events under an additive model for tumor grade, tumor stage, and early tumor recurrence. Among them, the synergistic effect toward portal vein invasion between OPN overexpression and ANXA1Os downregulation was the most striking one. Portal vein invasion, which is unique for the intrahepatic tumor metastasis of HCC even in the advanced stage, is the most crucial factor for early tumor recurrence after tumor resection and the most unfavorable prognostic factor. Therefore ANXA1Os, alone or in addition to OPN,[25] may serve as potential target for therapeutic intervention or treatment of HCC.

The cumulative effects of the three genetic alterations were also examined with regard to tumor progression. If the presence of the three genetic variants are counted quantitatively by treating each one equally, there are obvious trends of more genetic variants with advanced tumor progression in terms of all the progression markers. HCC samples with more genetic alterations are shown to exhibit more frequent high-grade tumor, portal vein invasion, and early tumor recurrence (all Ps<0.0001). It is noted that the majority of patients with HCCs showing all three alterations had portal vein invasion (73%) and early tumor recurrence (80%), significantly more frequent by 13-fold and 5-fold, respectively, than those without any of these events (5% and 15%, respectively). HCCs with more alterations also exhibited worse prognosis (P=0.000001), with a very low 10-year survival (7%) for those with all the three alterations, and better for those with two (22%), one (29%), and none (43%) of the genetic alterations. These findings indicate that the three aberrant expressions of the three genes contributed cooperatively to the metastatic potential of HCC, and hence high risk of early recurrence and poor prognosis. With the dramatic advancement in the understanding of human genome, the gene expression profile using molecular techniques, such as genome-wide microarray and quantitative RT-PCR, is now used to identify a gene expression signature to predict disease outcome in human cancer.[44,45] The combined analysis of the three genetic aberrations at 4q may help to discriminate tumor stage, risk of early recurrence and prognosis, and provided a model useful for molecular staging of HCC.

ANXA10s Nucleic Acids

The present invention includes an isolated or recombinant nucleic acid molecule encoding a polypeptide having at least one of the biological activities or having at least one expression characteristic of the novel short isoform of Annexin A10, termed Annexin 1Os (ANXA 10s). Quantitatively, ANXA1Os expression was found significantly lower in a human hepatocellular carcinoma (HCC) sample than a normal human tissue or sample.

The nucleic acid molecule may consist essentially of the nucleic acid sequence according to SEQ ID NO: 1 or may encode a polypeptide having an amino acid according to SEQ ID NO: 2 or a nucleic acid sequence encoding the amino acid sequence of an Annexin 1Os polypeptide. The nucleic acid sequence may include one or more additions, deletions or substitutions to SEQ ID NO: 1. The nucleic acid molecule preferably encodes a human ANXA10s polypeptide. ANXA10s nucleic acid molecules may also be identified in stomach of a variety of organisms including rat, mouse, bovine and other mammals.

The nucleic acid molecule may include cDNA, isolated genomic DNA, synthetic DNA, isolated mRNA and the like. In humans, ANXA 10s mRNA transcript was found to be higher in normal or control sample than in an HCC tissue sample. cDNA may be obtained from libraries prepared from mRNA isolated from various tissues expressing ANXA1Os. In humans, preferred tissue sources may be liver and stomach. Genomic DNA libraries encoding ANXA1 Os, such as genomic libraries containing Chromosome 4q may be commercially available from a variety of vendors. Synthetic DNA may be obtained by chemical synthesis of overlapping oligonucleotide fragments followed by assembly of the fragments to reconstitute part or all of the coding region and flanking sequences. RNA such as mRNA may be extracted from a tissue able to express ANXAIOs using standard molecular biology techniques and utilizing tools commercially available from Invitrogen (Carlsbad, Calif.) and Qiagen (Germany) and may be performed according to the manufacturers instructions or substantially as disclosed in the Examples.

The nucleic acid may encode a truncated form of a ANXAI Os polypeptide and may encode a fusion sequence or protein for the isolation or purification of an ANXAI0s protein. Truncated forms of ANXAI Os may include either N-terminus truncations or C-terminus truncations. Non-limiting examples of fusion protein sequences encompassed by the present invention encode those known in the protein purification arts such as Fc fusions, His-tag fusions and the like. Preferably a ANXAI0s fusion molecule significantly retains at least one function or characteristics of ANXAI0s. Fusion molecules may be cleaved or may remain fused.

ANXAIOs Vectors and Host Cells

The present invention also includes a ANXAI0s nucleic acid sequences operably linked to a promoter, an expression or delivery vector containing a ANXAIOs nucleic acid sequence operably linked to a promoter and a host cell transformed or transfected with at least one of the disclosed vectors. Nonlimiting examples of appropriate ANXA10s nucleic acid sequences include a sequence substantially similar to SEQ ID NO: 1 or a nucleic acid sequence that encodes the amino acid sequence according to SEQ ID NO: 2 or an ANXA10s polypeptide. The disclosed host cells and vectors may be used for expressing and isolating a ANXAI0s polypeptide. Protein expression may be performed using any technique known in the art such as but not limited to those disclosed in Methods of Enzymology, v. 185 Goeddel, D. V. ed. Academic Press (1990).

Host cells for the production of ANXAI0s include prokaryotic host cells, such as E. coli, yeast, plant, insect and mammalian host cells. Examples of suitable host cells may include COS, CHO, Hep 3B, HeLa and HCC cell lines. Mammalian host cells are preferred when post-translational modifications, such as glycosylation and polypeptide processing, are important for ANXAIOs activity. Mammalian expression allows for the production of secreted polypeptides, which may be recovered from growth media.

Vectors for the expression of ANXAIOs should contain sequences required for vector propagation and for expression of the cloned insert. The sequences may include a replication of origin, selection marker, promoter, ribosome binding site, enhancer or promoter sequence, RNA splice sites and/or a transcription termination site. Nonlimiting examples of vectors suitable for expression in the disclosed host cells are readily available from vendors such as Invitrogen (Carlsbad, Calif.) and Stratagene (San Diego, Calif.) and the like. Inserts or sequences encoding ANXAI0s may be operably linked to a promoter or inserted into vectors using standard recombinant DNA techniques known in the molecular biology arts. Vectors for tissue specific expression of ANXA10s are also included. Such vectors include promoters which function in liver or other desired organs in mice and viral vectors for the expression of ANXAI0s in targeted human cells such as but not limited to human liver cells or hepatocellular carcinoma.

Using the appropriate host-vector system, ANXAI0s may be produced recombinantly by culturing a host cell transformed or transfected with an expression vector containing a nucleic acid sequence encoding ANXA1Os under conditions such that ANXA1Os is produced, and isolating the product of expression. ANXA1Os may be produced in the supernatant of transfected mammalian cells or within transformed bacterial host cells.

The present invention also includes expression of ANXA1Os from endogenous nucleic acids by in vivo or ex vivo recombination events to allow modulation of ANXA1Os from the host chromosome, such as Chromosome 4q. Expression of ANXA1Os by the introduction of exogenous regulator sequences (e.g. promoters or enhancers) capable of directing the production of ANXA1Os from endogenous ANXA1Os coding regions is also encompassed. Stimulation of endogenous regulator sequences capable of directing ANXA1Os production (e.g. exposure to transcriptional enhancing factors) is also provided by the invention.

ANXA10s Polypeptide

The present invention also includes an ANXA1Os polypeptide, a novel short isoform of Annexin A1O. The ANXA1Os polypeptide lacks the 134 amino acid residues of the amino terminus of ANXA 10 and therefore lacks a calcium binding site commonly found in the Annexin family. FIG. 1 depicts a sequence comparison between ANXA1Os and Annexin A1O (ANXA 10). ANXA1Os was found to be expressed lower in HCC tissue samples than in normal or control liver tissue samples. The ANXA1Os may consist essentially of the amino acid sequence depicted in SEQ ID1 NO: 2 and may be less abundant in an HCC sample than a normal sample. Alternatively, ANXAI0s may include an ANXA1Os derivative such as a functional molecule substantially similar to SEQ ID NO: 2 but having amino acid deletions, additions or substitutions. The derivative will have at least one biological activity or characteristic of ANXAI0s.

The present invention also includes fusion polypeptides such as ANXA1Os-Fc fusions and the like. Fusions may be created for purification, tissue targeting or drug delivery.

The present invention also includes modifications to the ANXAI0s polypeptide. Modifications may include post-translational modifications (e.g. N-linked or O-linked carbohydrate chains, processing of N-terminal or C terminal ends), attachment of one or more chemical moieties to the amino acid backbone, chemical modifications of N-linked or O-linked carbohydrate chains. The polypeptides may be modified with a detectable label such as enzymatic, fluorescent, isotopic or affinity label for detection or isolation of the protein.

The polypeptides of the present invention may be isolated and purified from other polypeptides present in tissues, biological samples and cell lines. Purification may employ one or more standard protein purification steps used in the biochemical purification arts in an appropriate order to obtain purified protein. These steps may include chromatography steps such as but not limited to ion exchange, gel filtration, affinity chromography utilizing an anti-ANXA1Os antibody or biotin-streptavidin affinity complex and the like.

ANXAI0s polypeptides may be found in a variety of biological samples such as but not limited to blood, tissue, stomach tissue, liver tissue and the like. ANXAI0s is believed to be found in a lesser amount in an HCC sample than a normal sample.

An ANXAI0s polypeptide may be provided in a pharmaceutical form such as with a pharmaceutically acceptable diluent, carrier, solubilizer, emulsifier, preservative, adjuvant and the like. Administration of ANXAI0s pharmaceutical may increase the presence of ANXAI0s in the body or desired organ and may be provided as a therapy for the treatment of hepatocellular carcinoma or as a prophylactic measure against progression of hepatocellular carcinoma. Dose and administration of an ANXAI0s pharmaceutical may be determined using pharmacological methods known in the pharmacology arts such as but not limited to those provided in "Remington: The Science and Practice of Pharmacy", 20th edition, Gennaro (ed.) and Gennaro, Lippincott, Williams & Wilkins, 2000).

ANXA10s Antibodies

The present invention also includes a polyclonal or monoclonal antibody capable of specifically binding an ANXA1Os polypeptide or an epitope. The antibody may be any suitable antibody such as IgG, IgM, IgA, IgE, IgY and the like. Antigens for the generation of antibodies may be full-length polypeptides or peptides spanning a portion of the ANXA1Os sequence. Preferably an antibody against ANXA1Os or portion a thereof does not significantly detect ANXA 10 allowing discrimination between the two. Immunological procedures for the generation of polyclonal or monoclonal antibodies are known to one skilled in the art such as those disclosed in Harlow and Lane, *Antibodies: A Laboratory Manual*, Cold Spring Harbor Laboratory Press, N.Y. 1988. These procedures may be applied to the preparation of antibodies against ANXA1Os. Antibodies may be produced in a variety of hosts such as rabbit, rat, mouse, goat, chicken as well as others known in the antibody arts. A rabbit anti-ANXA1Os antibody has been generated that does not substantially bind ANXAI0. Additionally, antibodies may be generated to discriminate between ANXAI0s and ANXA 10 by creating an antibody cDNA expression library, using phage display to select for clones that bind ANXAI0s and not significantly to ANXA 10, and cloning or sequencing the desired clones. Alternatively, alone or in combination with the above methods, antibodies may be tested by immunohistological studies against stomach or liver of a particular organism such as human. As indicated, an antibody preferably substantially distinguishes between ANXAI0s and ANXA 10. Antibodies of the present invention may also include chimeric antibodies having variable and constant domain regions derived from different species such as for example a murine variable region and a human constant region or a murine constant region and a human variable region. Antibodies may be humanized using techniques known in the antibody arts.

Antibodies may be used in the affinity purification of ANXA1Os from a sample such as a biological sample or cell line. An antibody may be used to detect the presence of ANXA1Os or to quantitatively measure ANXA1Os in a sample such as blood, serum, liver, stomach, HCC tissue, an HCC cell line and the like.

The present invention also includes antibody fragments able to bind ANXAI0s such as Fab, Fab'2 or light chain fragments such as kappa or lamda light chain fragments. Antibody fragments may be produced by techniques known in the art such as cleaving an Fe portion from a whole antibody and retaining the Fab'2 portion or by cleaving one or more bonds such as disulfide bonds and retaining the portion able to bind ANXAI0s.

The present invention also includes methods of detecting an ANXA1Os polypeptide including incubating a sample suspected of containing an ANXAI0s polypeptide in the presence of an antibody of the present invention such as a polyclonal, monoclonal, chimeric or humanized antibody and detecting the bound antibody. Methods of detecting a polypeptide with an antibody such as those utilized in ELISA protocols are commonly known in the art and may include sandwich assays where a capture reagent and a detecting reagent are utilized or may not include a capture reagent.

Methods of Using ANXA10s

The present invention also includes methods of diagnosing a patient having or at risk of developing hepatocellular carcinoma (HCC). The method may include obtaining a biological sample from an individual suspected of having hepatocellular carcinoma, measuring the amount of ANXAIOs in the biological sample, comparing the amount of ANXA1Os to a control value or sample and determining the patient has or is at risk of developing hepatocellular carcinoma if the amount of ANXAI0s is less, such as but not limited to less, statistically less or significantly less, in the patient sample than in the control.

Patient samples may include any biological sample suspected of having or expressing a ANXAI0s polypeptide. Biological samples may include tissue samples such as a carcinoma tissue, liver tissue, stomach, blood, whole blood, serum, and the like. The methods of the present invention may detect or quantify the amount of an ANXA1Os polypeptide or an ANXAIOs nucleotide sequence. Polypeptide detection may be performed by using any known method utilized in polypeptide detection arts such incubating the sample in the presence of an antibody or antibody fragment able to bind ANXAI0s and detecting the bound antibody or antibody fragment. An ANXAI0s nucleotide sequence such as but not limited to an mRNA molecule may be detected or quantified by detecting or measuring a probe able to hybridize to ANXAI0s mRNA under stringent conditions as provided in the molecular biology arts or by techniques such as RT-PCR with appropriate primers such as those substantially provided in the Examples.

The amount of ANXAIOs in a patient sample may be compared to a control value or a control sample or a normal sample. A normal or control sample may be from an individual not having HCC and may include a tissue sample, a blood sample or any biological sample that includes ANXAI0s. A patient is at risk of developing hepatocellular carcinoma or is deemed to have hepatocellular carcinoma if the measured or detected ANXAI0s amount is lower, such as but not limited to lower, significantly lower or statistically lower, than that of the appropriate control value or sample.

The present invention also includes a method of diagnosing a patient with hepatocellular carcinoma including obtaining a biological sample from an individual suspected of having or at risk of developing hepatocellular carcinoma (HCC), measuring an amount of ANXA1Os, osteopontin (OPN) and alpha-fetoprotein (AFP) in the biological sample, comparing the measured amount or presence of ANXA1Os, OPN or AFP to a corresponding control ANXAI0s, OPN or AFP value or sample and determining the patient is at risk of developing hepatocellular carcinoma if the amount of ANXAI0s is lower in the patient sample than the control value or sample, and the amount of OPN and AFP is higher in the patient sample than in the control value or sample. The method may include detecting or measuring nucleic acids such as by utilizing RT-PCR or a polypeptide or amino acid sequence such as by utilizing an antibody.

The present invention also includes a method of staging the progression of hepatocellular carcinoma in a patient including obtaining a biological sample from an individual suspected of having or developing hepatocellular carcinoma, measuring a level of gene expression or mRNA transcript in a sample of each of ANXAI0s, osteopontin (OPN) and alpha-fetoprotein (AFP), comparing the levels of gene expression or mRNA transcript to a corresponding control ANXAI0s, OPN, and AFP value or gene expression level or mRNA transcript, determining an expression profile indicative of the comparisons and comparing the expression profile to a predetermined set of data corresponding to hepatocellular tumor progression.

Gene expression or mRNA transcript measurement may utilize or incorporate any appropriate technique known in the molecular biology arts for measuring gene expression or quantifying rmRNA transcripts such as reverse transcription polymerase chain reaction (RT-PCR), microarrays, Southern blots and the like. Primers or oligos specific to ANXAI0s, ANXAI0, OPN and AFP may be utilized and non-limiting examples of such may be found in the Examples. Oligos may include an appropriate detectable label attached thereto.

Primers such as a 5' primer and a 3' primer may be generated by examination of the appropriate sequence, using primer design software programs and oligo synthesizing techniques known in the molecular biology arts. 5' and 3' primers may be developed for ANXAI0s, ANXA10, OPN and AFP as well as appropriate controls. Non-limiting examples of appropriate primers may be found in the Examples.

Control values or samples may be obtained by measuring the amount of ANXA1Os, OPN or AFP in an individual or group of individuals not suffering from hepatocellular carcinoma. Alternatively control values may be within the same patient but in a different tissue or biological sample.

EXAMPLES

The following examples are to illustrate various aspects and benefits of the disclosed invention and are not intend as limiting features and therefore should not be construed as limiting the claims.

Example 1

Preparation of Tissue Samples and Tumor Staging

Tissue Samples. Between 1987 and 1997, 909 surgically resected primary HCCs were pathologically assessed at the National Taiwan University Hospital. Of these, 294 unifocal primary HCCs, as previously descn'bed, 18'26-30 With complete clinicopathological assesement and examined for mRNA levels of AFP, OPN, ANXA1O and ANXAI0s formed the basis of this study provided in these Examples.

Histologic Study and Tumor Staging. The tumor grade was classified into four grades: grade I (65 cases), grade II (123 cases), grade III (81 cases), and grade IV (25 cases). At the time of operation, no evidence of regional lymph node or distant metastasis was noted. HCC with complete fibrous encapsulation has a favorable prognosis, regardless of tumor size 26 and vascular invasion is a crucial unfavorable prognostic factor. 14,29 Hence, a modified tumor staging was adopted, with special emphasis on the extent of vascular invasion, as previously described. 14,15,31 Stage I to II HCCs had no vascular invasion, whereas stage IIIA to IV HCCs had various extent of vascular invasion. Stage I HCC included encapsulated minute HCC; . . . , 2 cm without liver or vascular invasion (9 cases). Stage II HCC (123 cases) included minute HCC with liver invasion or minute satellite close to the main tumor (10 cases); or larger HCC with (56 cases) or without liver invasion (57 cases), but no microvascular invasion. Stage IIIA HCC had microinvasion of thin-walled vessels in the tumor capsule or nearby satellite (47 cases). Stage IIIB HCC had limited invasion of the small portal vein branch near the main tumor (38 cases). Stage IV HCC had invasion of major portal vein branches, satellites extending deeply 20 into the surrounding liver, tumor rupture, or invasion of the adjacent organs (77 cases). The pathological stage correlated closely with patient prognosis, as previously described.[14,15,31]

Early Tumor Recurrence. The diagnosis of tumor recurrence and metastasis was based on imaging examinations with ultrasonography and/or computed tomography, supplemented with X-ray, bone scan, and serum a-fetoprotein (AFP) elevation, as described elsewhere.[14,15,31] Until the end of February 2004 with a follow-up observation up to 180 months, 268 patients were eligible for the evaluation of tumor recurrence. Twenty patients who died within one year after tumor resection and were negative for tumor recurrence or metastasis were excluded, including 6 died within one month. Another 6 cases who died in the second year and had no information about tumor recurrence were also excluded.

Example 2

Identification of the Novel Short Isoform, Annexin 1Os

Screening of a cDNA library and Rapid Amplification of 5' and 3' cDNA Ends (RACE PCR). The liver cDNA library was constructed using polyadenylated mRNA extracted and purified from a normal adult liver by Oligotex-dT (Qiagen GmbH, Hilden, Germany). Double-stranded cDNA was synthesized and cloned into Uni-Zap XR vector using ZAP-cDNA Synthesis Kit (Stratagene, La Jolla, Calif.). The ANXA1O cDNA probe (from 848 to 1308 nt, GI:9625245) labeled by PCR DIG Probe Synthesis Kit was used for cDNA library screen and detected by DIG Luminescent Detection Kit (Roche Applied Science, Penzberg, Germany) according to the recommendations of the manufacturer. Approximately 2×106 phages were screened, and positive plaques were selected for in vivo excision to generate the pBluescript phagemid from the Uni-ZAP vector. The inserts were sequenced by ABI auto sequencer.

Example 3

Quantitative Analysis of AFP, OPN, ANXA10 AND ANXAIOs

Reverse Transcription-Polymerase Chain Reaction (RT-PCR). The large-scale quantitative analysis of AFP, OPN, ANXAI0, and ANXAIOs mRNAs was done by RTPCR assays using porphobilinogen deaminase (PBGD) or S26 ribosomal protein mRNA for internal controls, as described previously.14,15 Briefly, total RNA samples (2 ug) from paired tumor and nontumor liver tissues were reverse transcribed with 200 units MMLV reverse transcriptase (BRL, Bethesda, Md.) in a volume of 20 J . . . 1 I to generate the first strand cDNA. For PCR, 2 J . . . 1 I RT product, 1.25 unit Pro Taq polymerase (protech Technology Enterprise Co, Taipei, Taiwan), 1× Pro Tag buffer, 200 J . . . 1M each dGTP, dTTP, dATP and dCTP were mixed with 0.2 J . . . 1M primers in a total volume of 30 ul. AFP eDNA was amplified using AFP-F38 (5'-CTAGCAACCARGAAGTGGGTG-3'), also provided as SEQ ID NO: 9, and AFP-R558 (5'-GATGCCTTCT-TGCTATCTCAT-3'), also provided as SEQ ID NO: 10 primers with an initial heating at 94° C. for 2 min, followed by 23 cycles of touchdown PCR (94° C. for 30 s, annealing temperature for 1 min, 72-c for I min; the annealing temperature was begun at 65° C. and reduced by 1" C per two 5 cycles for the first 20 cycles, until 55° C., then 3 additional cycles at 55 DC). The PCR was stopped at 28, 22, 32 and 32 cycles for AFP, OPN, ANXAI0, and ANXAI Os, respectively, and at 22 cycles for S26 and 28 cycles for PBGD. The products were electrophoresed on 2% agarose gel, the concentration of the PCR fragments were detected by the ID Imaging Analysis Software (Kodak Digital Science, USA).

The primers used for OPN cDNA were OPN-A (CCCT-TCCAAGTAAGTCCAACGAAAGCC), also provided as SEQ ID NO: 7, and OPN-F (GCTGACTCGTTTCATAACT-GTCCTTCCC), also provided as SEQ ID NO: 8, and the primers common for ANXAI0 and ANXAI0s were ANXAI0-3A (TTGTTCCTCTGTGTTCGAGACAAACC), and ANXAI0-4B (5'-GTAGGCAAATTCAGGATAGTAGGC), as described. 14, 15 The primers specific for ANXAI0 were A10-IA (CCTTAATTCTTTCTGGCTTCACAGT), also provided as SEQ ill NO: 5, and AI0-2B (CAATTCTCATCAGT-GCCTACTCC), also provided as SEQ ill NO: 6 for ANXA1O, and those primers specific for ANXA1Os were A1Os-F1 (CTCAAAACACACTGATACATAGTTC), also provided as SEQ ill NO: 3, and A10-20 3B (GGTTTGTCTC-GAACACAGAGAACAA), also provided as SEQ ID NO: 4. The primers for PBGD and the S26 ribosomal protein mRNA were PBGD-5' (TGTCTGGTAACGGCAATGCGGCT), also provided as SEQ ID NO: 11, and PBGD3' (GGTCCACT-TCATTCTTCTCCAGG), also provided as SEQ ID NO: 12; and S26F (CCGTGCCTCCAAGATGACAAAG), also provided as SEQ ID NO: 13, and S26R (5'-GTTCGGTCCT-TGCGGGCTTCAC-3'), also provided as SEQ ID NO; 14, respectively.[14,15]

Example 4

Results of Study

Clinical and Pathological Features of 294 Study Cases with Unifocal Primary HCC

These patients, 231 males and 63 females, represented a group of HCC patients, who had adequate liver function reserve and received total surgical resection of the primary tumors, 29 and none received transhepatic arterial embolization (TAE) or chemotherapy before surgery. The age of the patients ranged from 14 to 88 years (mean age: 55.9 years). Serum hepatitis B surface antigen (HBsAg) was detected in 203 cases, anti-HCV antibody in 94 cases, including 27 cases also positive for HBsAg, and 24 were negative for both (8.2%).

Expression of Annexin 10s (ANXA10s), a Novel Short Isoform of ANXA10, in Liver

Figure 2:
FIG. 2 is an image of an agarose gel depicting reverse-transcription-polymerase chain reaction (RT-PCR) measurements of a-fetoprotein (AFP), osteopontin (OPN), and the novel short isoform of Annexin A1O, termed Annexin 1Os (ANXA1Os), in a hepatocellular carcinoma (H) and a normal or control liver (L).

With RT-PCR we could directly clone the nearly full-length cDNA of ANXA1O from Hep3B I5 and HeLa, but failed to do so in the nontumorous liver. To determine the potential existence of isoforms of ANXA1O, we used liver cDNA library screen and cloned a novel short isoform of Annexin A1O (designated as ANXA1Os) instead of ANXA1O. ANXA1Os uses an alternative start site in the intron 5 and the cDNA encodes a truncated protein lacking the amino-terminal 134 amino acid residues, and hence lacking the first and the major part of the second repeats of the core domain. The structure of ANXA10s thus fundamentally deviates from that of the Annexin family, which classically has 4 repeats (FIG. 1; GenBank AY626137). Using primer sets specific for ANXA1O and ANXA10s, we found that ANXA10s was expressed in constitutive pattern in the adult liver as shown in FIG. 2. In contrast, ANXA10, which was cloned from Hep3B and HeLa cell, 15 was expressed in stomach and gastric cancer, and a few HCCs and HCC cell lines (data not shown), but not in the nontumor liver (data not shown).

Individual Aberrant Gene Expression in Association with Tumor Progression

Of the 294 unifocal primary HCCs, AFP overexpression, OPN overexpression, and ANXA1Os downregulation were found in 150 (51%), 157 (53%) and 176 (60%), respectively (FIG. 2). To elucidate their roles in the tumor progression of HCC, we correlated the three aberrant gene expressions with major clinicopathological features associated with tumor progression, including tumor grade, tumor stage, and early tumor recurrence. For individual aberrant gene expression, AFP overexpression, OPN overexpression and ANXA 10s downregulation were associated with more frequent grades II to IV tumors, stages IIIB-IV HCCs, and early tumor recurrence (all Ps<0.0001 and all ORs>1.0) (Table 1). It was important to note that HCC with AFP overexpression, OPN overexpression or ANXA1 Os downregulation had a more than two-fold increase in portal vein invasion (stages IIIB to IV) and early tumor recurrence as compared with those expressed normally. All the odds ratios exceeded 1.0. The magnitude of odds ratio of ANXA10 downregulation is higher than those of the AFP and OPN overexpression in tumor progression.

Figure 3:
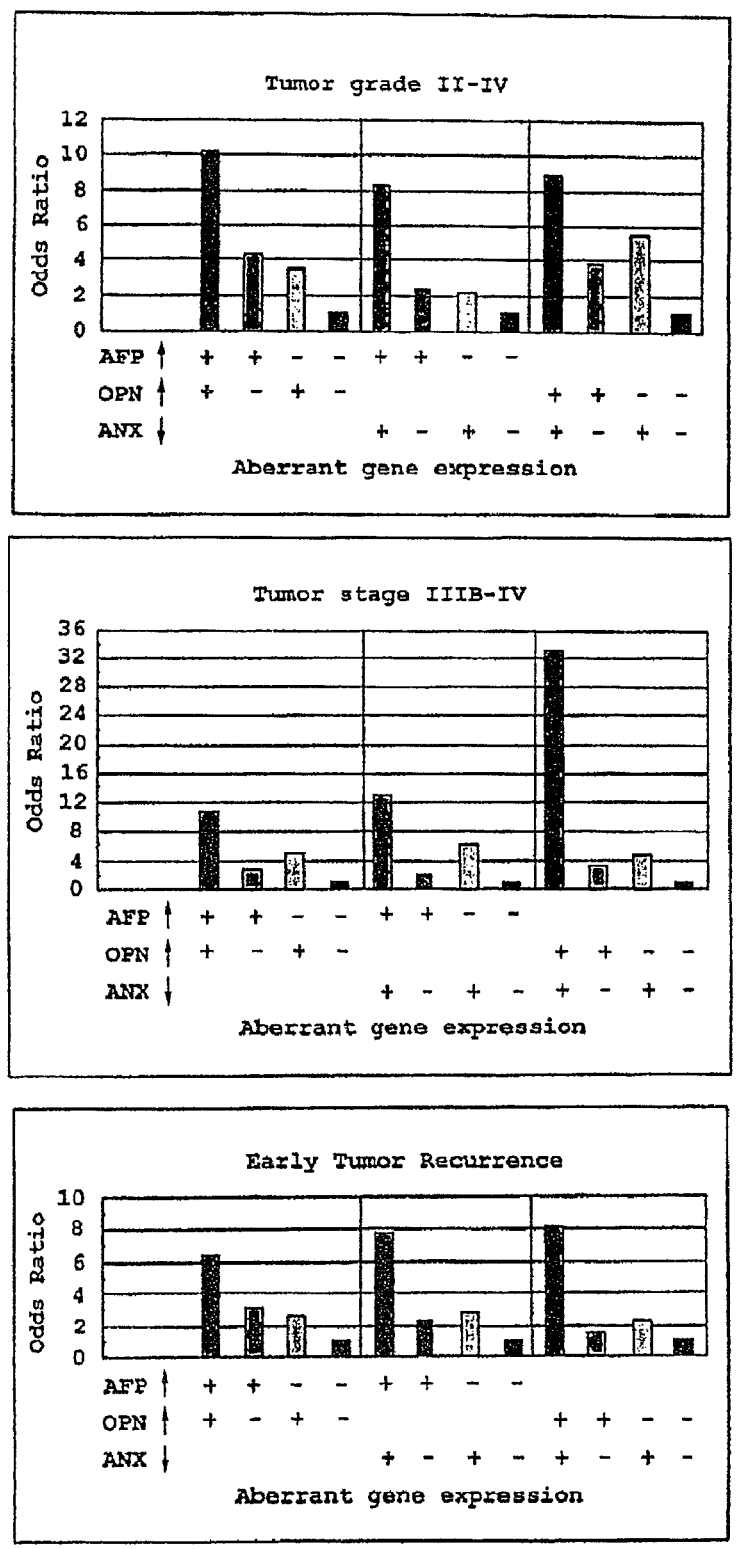
FIG. 3 is a graph depicting odds ratios (ORs) for tumor grade II-IV, tumor stage IIIB-IV, and early tumor recurrence, respectively, for the pairwise combinations of the presence of aberrant gene expressions of a-fetoprotein (AFP) overexpression, osteopontin (OPN) overexpression, and annexin A10s (ANXA10s) downregulation. ↑ and ↓ designate overexpression and downregulation, respectively. + and − designate yes and no, respectively.
Figure 4:
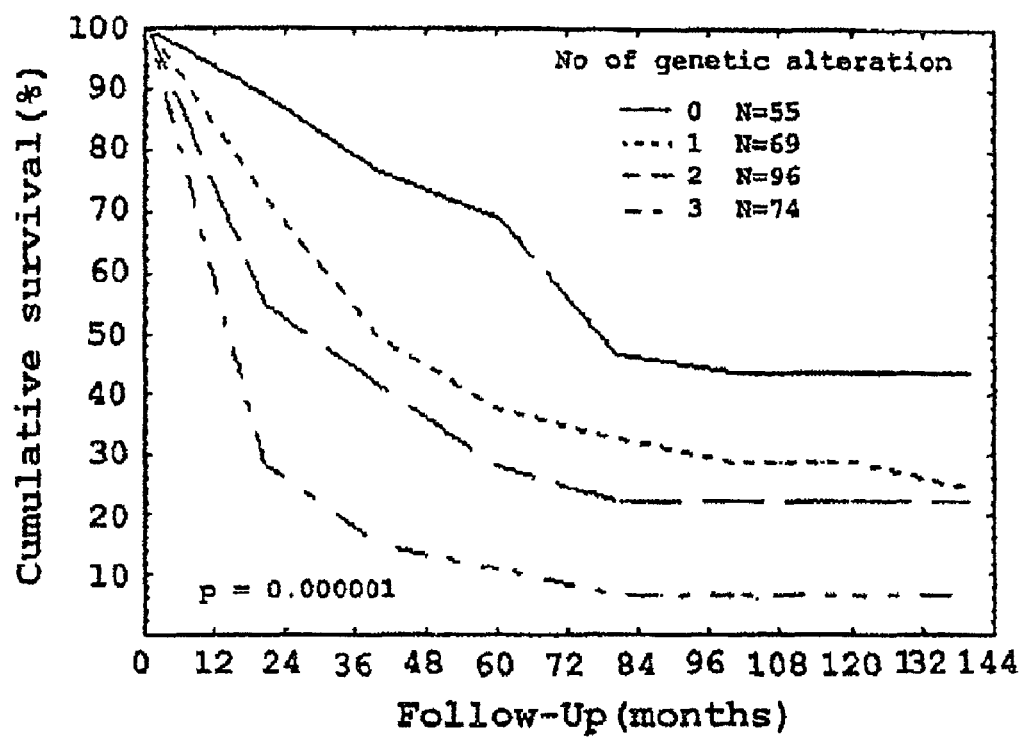
FIG. 4 is a graph depicting the number of genetic alterations (o-fetoprotein 10 overexpression, osteopontin overexpression, and annexin A10s downregulation) in relation to cumulative survival of 294 patients receiving surgical resection of unifocal primary hepatocellular carcinoma (HCC). HCCs with more genetic alterations had worse survival. Log-Rank test, P=0.000001.

Interaction Between Aberrant Gene Expressions in Tumor Progression and Prognosis As all the three genes are located at chromosome 4q that exhibits high frequency of allelic loss in HCC, we analyzed the potential interrelations of the three aberrant gene expressions in relation to tumor progression of HCC. As shown in FIG. 2, AFP overexpression correlated positively with OPN overexpression (P=0.0026) and ANXA10S downregulation (P=0.00001), while OPN overexpression was associated with more frequent ANXA10s downregulation (P=O.OOOO1). We then did a pair-wise analysis. As shown in Table 3, a combination of any two of these genetic aberrations (AFP overexpression and OPN overexpression, AFP overexpression and ANXA1Os downregulation, OPN overexpression and ANXA1Os downregulation) revealed more frequent high tumor grade, high tumor stage and early tumor recurrence (all Ps<0.0001). As illustrated in FIG. 3, the magnitude of odds ratio for those with the presence of two genetic variants exceeded the projected sum of the solely presence of single variant. i.e., there were apparently interactive effects between these genetic variants under an additive model. In particular, OPN overexpression and ANXA1Os downregulation exhibited a dramatically synergistic effect toward portal vein invasion, with an odds ratio of 33.2 as compared with HCCs with one (OR:3.1 to 4.5) and none (OR, 1.0) of the two genetic aberrant expressions. With the apparent interaction between these genetic alterations, we therefore analyzed their cumulative effects in tumor progression. As shown in Table 4, HCCs with more genetic aberrations showed more frequent high tumor grade, portal vein tumor invasion (stage IIIB and IV), and early tumor recurrence (all Ps<O.OOOI). The majority of HCCs with all three alterations had portal vein invasion (73%), more than 13 fold higher than those with none of the three events (5%), and more early tumor recurrence (5-fold). HCCs with more genetic alterations also showed worse prognosis, 5 P=O.OOOOO1 (FIG. 4), with the lowest 10-year survival for those with all the three aberrant expressions (7%), better for those with two (22%), one (29%), and the highest for those with none of these changes (43%).

All publications, including patent documents and scientific articles, referred to in this document including the bibliography and attachments are incorporated by reference in their entirety for all purposes to the same extent as if each individual publication were individually incorporated by reference. All headings are for the convenience of the reader and should not be used to limit the meaning of the text that follows the heading, unless so specified.

REFERENCES

1. Marchio A, Meddeb M, Pineau P, Danglot G, Tiollais P, Bemheim A, Dejean A. Recurrent chromosomal abnormalities in hepatocellular carcinoma detected by comparative genomic hybridization. Genes Chromosomes Cancer 1997; 18:59-65.
2. Kusano N, Shiraishi K, Kubo K, Oga A, Okita K, Sasaki K. Genetic aberrations detected by comparative genomic hybridization in hepatocellular carcinomas: their relationship to clinicopathological features. Hepatology 1999; 29: 1858-1862.
3. Wong N, Lai P, Lee S W, Fan S, Pang E, Liew C T, Sheng Z, Lau J W, Johnson P J. Assessment of genetic changes in hepatocellular carcinoma by comparative genomic hybridization analysis: relationship to disease stage, tumor size, and cirrhosis. Am J Pathol 1999; 154:37-43.
4. Wong N, Lai P, Pang E, Fung L F, Sheng Z, Wong V, Wang W, Hayashi Y, Perlman E, Yuna S, Lau J W, Johnson P J. Genomic aberrations in human hepatocellular carcinomas of differing etiologies. Clin Cancer Res 2000; 6:4000-4009.
5. Guan X Y, Fang Y, Sham J S, Kwong D L, Zhang Y, Liang Q, Li H, Zhou H, Trent J M. Recurrent chromosome alterations in hepatocellular carcinoma detected by comparative genomic hybridization. Genes Chromosomes Cancer 2000; 29:110-116.
6. Chou Y R, Chung K C, Jeng L B, Chen T C, Liaw Y F. Frequent allelic loss on chromosomes 4q and 16q associated with human hepatocellular carcinoma in Taiwan. Cancer Lett 1998; 123:1-6.
7. Bando K, Nagai H, Matsumoto S, Koyama M, Kawamura N, Onda M, Emi M: Identification of a I-eM region of common deletion on 4q35 associated with progression of hepatocellular carcinoma. Genes Chromosomes Cancer 1999, 25:284289.
8. Yeh S H, Chen P J, Lai M Y, Chen D S: Allelic loss on chromosomes 4q and 16q in hepatocellular carcinoma: association with elevated alpha-fetoprotein production. Gastroenterology 1996, 110:184-192.
9. McGowan-Jordan I J, Speevak M D, Blakey D, Cevrette M: Suppression of tumorigenicity in human teratocarcinoma cell line PA-1 by introduction of chromosome 4. Cancer Res 1994, 54:2568-2572.
10. Kuroki T, Fujiwara Y, Tsuchiya E, Nakamori S, Imaoka S, Kanematsu T, Nakamura Y. Accumulation of genetic changes during development and progression of hepatocel- 10. lular carcinoma: loss of heterozygosity of chromosome arm 1p occurs at an early stage of hepatocarcinogenesis. Genes Chromosomes Cancer 1995; 13:163-167.
11. Piao Z, Park C, Park J H, Kim H. Deletion mapping of chromosome 4q in hepatocellular carcinoma. Int J Cancer 1998; 79:356-360.
12. Laurent-Puig P, Legoix P, Bluteau 0, Belghiti J, Franco D, Binot F, Monges G, Thomas G, Bioulac-Sage P, Zucman-Rossi J. Genetic alterations associated with hepatocellular carcinomas define distinct pathways of hepatocarcinogenesis. Gastroenterology 2001; 120:1763-1773.
13. Zondervan P E, Wink J, Alers J C, Uzermans J N, Schalm S W, de Man R A, van Dekken H. Molecular cytogenetic evaluation of virus-associated and non-viral hepatocellular carcinoma: analysis of 26 carcinomas and 12 concurrent dysplasias. J Patho 12000; 192:207-215.
14. Pan H W, Ou Y R, Peng S Y, Liu S H, Lai P L, Lee P H, Sheu J C, Chen C L, Hsu He. Overexpression of osteopontin is associated with intrahepatic metastasis, early recurrence, and poorer prognosis of surgically resected hepatocellular carcinoma. Cancer 2003; 98:119-127.
15. Liu S H, Lin C Y, Peng S Y, Jeng Y M, Pan H W, Cheng W, Kuo M Y P, Hsu He. Downregulation of Annexin A10 in hepatocellular carcinoma is associated with vascular invasion, early recurrence, and poor prognosis in synergy with p53 mutation. Am J Pathol 2002; 160:1831-1837.
16. Abelev G I. Alpha-fetoprotein in ontogenesis and its association with malignant tumors. Cancer Res 1971; 14:295-358.
17. Chen D S, Sung J L. Serum alphafetoprotein in hepatocellular carcinoma. Cancer 1977; 40:779-783.
18. Peng S Y, Lai P L, Chu J S, Lee P H, Tsung P T, Chen D S, Hsu H C. Expression and hypomethylation of alpha-fetoprotein gene in unicentric and multicentric human hepatocellular carcinomas. Hepatology 1993; 17:35-41.
19. Wang X W, Xu B. Stimulation of tumor-cell growth by alpha-fetoprotein. Int J Cancer 1998; 75:596-599.
20. Li M S, Li P F, Yang F Y, He S P, Du G G, Li G. The intracellular mechanism of alphafetoprotein promoting the proliferation of NIH 3T3 cells. Cell Res 2002; 12:151-156.
21. Li M S, Li P F, He S P, Du G G, Li G. The promoting molecular mechanism of alphafetoprotein on the growth of human hepatoma. Be17402 cell line. World J Gastroenterol 2002; 8:469-475.
22. Mizejewski G J. Biological role of alpha-fetoprotein in cancer: prospects for anticancer therapy. Expert Rev Anticancer Ther 2002; 2:709-735.
23. Nomura F, Ohnishi K, Tanabe Y. Clinical features and prognosis of hepatocellular carcinoma with reference to serum alpha-fetoprotein levels: analysis of 606 patients. Cancer 1989; 64:1700-1707.
24. Gotoh M, Sakamoto M, Kanetaka K, Chuuma M, Hirohashi S. Overexpression of osteopontin in hepatocellular carcinoma. Pathol Int 2002; 52:19-24.
25. Ye Q H, Qin L X, Forgues M, He P, Kim J W, Peng A C, Simon R, Li Y, Robles A I, Chen Y, Ma Z C, Wu Z Q, Ye S L, Liu Y K, Tang Z Y, Wang X W. Predicting hepatitis B virus-positive metastatic hepatocellular carcinomas using gene expression profiling and supervised machine learning. Nat Med 2003; 9:416-423.
26. Hsu H C, Wu T T, Wu M Z, Sheu I C, Lee C S, Chen D S. Tumor Invasiveness and prognosis in resected hepatocellular carcinoma: Clinical and pathological implications. Cancer 1988; 61:2095-2099.
27. Hsu H C, Chiou T I, Chen Z Y, Lee C S, Lee P H, Peng S Y. Clonality and clonal evolution of hepatocellular carcinoma with multiple nodules. Hepatology 1991; 13:923-928.
28. Hsu H C, Tseng H I, Lai P L, Lee P H, Peng sv. Expression of p53 gene in 184 unifocal hepatocellular carcinomas: association with tumor growth and invasiveness. Cancer Res 1993; 53: 4691-4694.
29. Hsu H C, Jeng Y M, Mao T L, Chu I S, Lai P L, Peng S Y. I3-Catenin mutations are associated with a subset of low stage hepatocellular carcinoma negative for hepatitis B virus and with favorable prognosis. Am 1 Pathol 2000; 157:763-770.
30. Hsu H C, Peng S Y, Lai P L, Chu I S, Lee P H. Mutations of p53 gene in hepatocellular carcinoma (HCC) correlate with tumor progression and patient prognosis: a study of 138 patients with unifocal HCC. Int 1 Oncol 1994; 4:1341-1347.
31. Peng S Y, Chen W I, Lai P L, Ieng Y M, Sheu I C, Hsu H C. Association of high afetoprotein level with high stage, early recurrence and poor prognosis of hepatocellular carcinoma: Significance of hepatitis B virus infection, age, p53 and 13 catenin mutations. Int 1 Cancer 2004; Vol. 112 (in press)
32. Deloukas P, et al. (>40 authors). A physical map of 30,000 human genes. Science 1998, 282:744-746.
33. Dudich E, Semenkova L, Gorbatova E, Dudich I, Khromykh L, Tatulov E, Grechko G, Sukhikh G. Growth-regulative activity of human a-fetoprotein for different types Of tumor and normal cells. Tumour Biol 1998; 19:30-40.
34. Imamura H, Matsuyama Y, Tanaka E, Ohkubo T, Hasegawa K, Miyagawa S, Sugawara Y, Minagawa M, Takayama T, Kawasaki S, Makuuchi M. Risk factors contributing to early and late phase intrahepatic recurrence of hepatocellular carcinoma after hepatectomy. 1 Hepatol 2003; 38:200-207.
35. Li Y, Tang Z Y, Ye S L, Liu Y K, Chen 1, Xue Q, Chen 1, Gao D M, Bao W H. Establishment of cell clones with different metastatic potential from the metastatic hepatocellular carcinoma cell line MHCC97. World 1 Gastroenterol 2001; 7:630-636.
36. Craig A M, Bowden G T, Chambers A F, et al. Secreted phosphoprotein mRNA is induced during multi-stage carcinogenesis in mouse skin and correlates with the metastatic potential of murine fibroblasts. Int 1 Cancer 1990; 46:133-137.
37. Behrend E I, Craig A M, Wioson S M, Denhardt D T, Chambers A F. Reduced malignancy of ras-transformed NIH 3T3 cells expressing antisense osteopontin RNA. Cancer Res 1994; 54:832-837.
38. Tuck A B, Arsenault D M, O'Malley F P, Hota C, Ling M C, Wilson S M, Chambers A F. Osteopontin induces increased invasiveness and plasminogen activator expression of human mammary epithelial cells. Oncogene 1999; 18:423 7-4246.
39. E I-Tanani M, Barraclough R, Wilkinson M C, Rudland P S. Metastasis-inducing dna regulates the expression of the osteopontin gene by binding the transcription factor tcf-4. Cancer Res 2001; 61:5619-5629.
40. Medico E, Gentile A, Lo Celso C, Williams T A, Gambarotta G, Trusolino L, Comoglio P M. Osteopontin is an autocrine mediator of hepatocyte growth factor induced invasive growth. Cancer Res 2001; 61:5861-5868.
41. Morgan R O, Jenkins N A, Gilbert D J, Copeland N G, Balsara B R, Testa J R, Fernandez M P. Novel human and mouse annexin A1O are linked to the genome duplications during early chordate evolution. Genomics 1999; 60:40-49.
42. Morgan R O, Fernandez M P: Annexin gene structures and molecular evolutionary genetics. Cell Mol Life Sci 1997, 53: 508-515.
43. Moss S E, Morgan R O. The annexins. Genome Bioi 2004; 5:219.1-219.8.
44. van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer. Nature 2002; 415:530-536.
45. Ma X J, Salunga R, Tuggle J T, Gaudet J, Enright E, McQuary P, Payette T, Pistone M, Stecker K, Zhang B M, Zhou Y X, Vamholt H, Smith B, Gadd M, Chatfield E, Kessler J, Baer T M, Erlander M G, Sgroi D C. Gene expression profiles of human breast cancer progression. Proc Nat! Acad Sci USA. 2003; 100:5974-5799.

What is claimed is:

1. An isolated nucleic acid molecule consisting essentially of:
   a) the nucleic acid sequence according to SEQ ID NO: 1
   b) the nucleic acid sequence encoding the amino acid sequence according to SEQ ID NO: 2; or
   c) a nucleic acid sequence encoding the amino acid sequence of annexin 10s (ANXA10s) polypeptide.

2. The nucleic acid molecule according to claim 1, wherein said nucleic acid molecule is selected from the group consisting of cDNA, synthetic DNA, and isolated mRNA.

3. The isolated nucleic acid molecule according to claim 2, wherein said mRNA is more abundant in a normal liver cell than a hepatocellular carcinoma cell.

4. An isolated expression vector comprising the nucleic acid sequence of claim 1, operably linked to a promoter.

5. An isolated host cell transfected with the expression vector according to claim 4.

6. The isolated host cell of claim 5, wherein said host cell is a eukaryotic cell or a prokaryotic cell.

* * * * *

SEQUENCE LISTING

<160> NUMBER OF SEQ ID NOS: 17

<210> SEQ ID NO 1
<211> LENGTH: 910
<212> TYPE: DNA
<213> ORGANISM: Homo sapiens

<400> SEQUENCE: 1

```
ctcaaaacac actgatacat agttctataa taaatcatac ctttaacatg ttttcttata      60
cagaatacag caataacctc caagaggaca tttattcaga gacctcagga cacttcagag     120
atactctcat gaacttggtc caggggacca gagaggaagg atatacagac cctgcgatgg     180
ctgctcagga tgcaatggtc ctatgggaag cctgtcagca gaagacgggg gagcacaaaa     240
ccatgctgca aatgatcctg tgcaacaaga gctaccagca gctgcggctg gttttccagg     300
aatttcaaaa tatttctggg caagatatgg tagatgccat taatgaatgt tatgatggat     360
actttcagga gctgctggtt gcaattgttc tctgtgttcg agacaaacca gcctattttg     420
cttatagatt atatagtgca attcatgact ttggtttcca taataaaact gtaatcagga     480
ttctcattgc cagaagtgaa atagacctgc tgaccataag gaaacgatac aaagagcgat     540
atggaaaatc cctatttcat gatatcagaa attttgcttc agggcattat aagaaagcac     600
tgcttgccat ctgtgctggt gatgctgagg actactaaaa tgaagaggac ttggagtact     660
gtgcactcct ctttctagac acttccaaat agagattttc tcacaaattt gtactgttca     720
tggcactatt aacaaaacta tacaatcata ttttctcttc tatctttgaa attattctaa     780
gccaaagaaa actatgaatg aaagtatatg atactgaatt tgcctactat cctgaatttg     840
cctactatct aatcagcaat taaataaatt gtgcatgatg gaataataga aaaaaaaaaa     900
aaaaaaaaaa                                                           910
```

<210> SEQ ID NO 2
<211> LENGTH: 196
<212> TYPE: PRT
<213> ORGANISM: Homo sapiens

<400> SEQUENCE: 2

```
Met Phe Ser Tyr Thr Glu Tyr Ser Asn Asn Leu Gln Glu Asp Ile Tyr
1               5                   10                  15

Ser Glu Thr Ser Gly His Phe Arg Asp Thr Leu Met Asn Leu Val Gln
            20                  25                  30

Gly Thr Arg Glu Glu Gly Tyr Thr Asp Pro Ala Met Ala Ala Gln Asp
        35                  40                  45

Ala Met Val Leu Trp Glu Ala Cys Gln Gln Lys Thr Gly Glu His Lys
    50                  55                  60

Thr Met Leu Gln Met Ile Leu Cys Asn Lys Ser Tyr Gln Gln Leu Arg
```

```
                65                  70                  75                  80
Leu Val Phe Gln Glu Phe Gln Asn Ile Ser Gly Gln Asp Met Val Asp
                    85                  90                  95
Ala Ile Asn Glu Cys Tyr Asp Gly Tyr Phe Gln Glu Leu Leu Val Ala
                100                 105                 110
Ile Val Leu Cys Val Arg Asp Lys Pro Ala Tyr Phe Ala Tyr Arg Leu
            115                 120                 125
Tyr Ser Ala Ile His Asp Phe Gly Phe His Asn Lys Thr Val Ile Arg
        130                 135                 140
Ile Leu Ile Ala Arg Ser Glu Ile Asp Leu Leu Thr Ile Arg Lys Arg
145                 150                 155                 160
Tyr Lys Glu Arg Tyr Gly Lys Ser Leu Phe His Asp Ile Arg Asn Phe
                165                 170                 175
Ala Ser Gly His Tyr Lys Lys Ala Leu Leu Ala Ile Cys Ala Gly Asp
                180                 185                 190
Ala Glu Asp Tyr
        195

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
ctcaaaacac actgatacat agttc                                             25

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
ggtttgtctc gaacacagag aacaa                                             25

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
ccttaattct ttctggcttc acagt                                             25

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
caattctcat cagtgcctac tccc                                              24

<210> SEQ ID NO 7
<211> LENGTH: 27
<212> TYPE: DNA
<213> ORGANISM: Artificial Sequence
```

```
<220> FEATURE:
<223> OTHER INFORMATION: Synthetic Construct

<400> SEQUENCE: 7
cccttccaag taagtccaac gaaagcc                                          27

<210> SEQ ID NO 8
<211> LENGTH: 28
<212> TYPE: DNA
<213> ORGANISM: Artificial Sequence
<220> FEATURE:
<223> OTHER INFORMATION: Synthetic Construct

<400> SEQUENCE: 8
gctgactcgt ttcataactg tccttccc                                         28

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
ctagcaacca rgaagtgggt g                                                21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
gatgccttct tgctatctca t                                                21

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
tgtctggtaa cggcaatgcg gct                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
ggtccacttc attcttctcc agg                                              23

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
ccgtgcctcc aagatgacaa ag                                               22
```

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
gttcggtcct tgcgggcttc ac                                          22

<210> SEQ ID NO 15
<211> LENGTH: 947
<212> TYPE: DNA
<213> ORGANISM: Homo sapiens

<400> SEQUENCE: 15
ctcaaaacac actgatacat agttctataa taaatcatac ctttaacatg ttttcttata    60
cagaatacag caataacctc caagaggaca tttattcaga gacctcagga cacttcagag   120
atactctcat gaacttggtc caggggacca gagaggaagg atatacagac cctgcgatgg   180
ctgctcagga tgcaatggtc ctatgggaag cctgtcagca aagacgggg gagcacaaaa    240 ccatgctgca aatgatcctg tgcaacaaga gctaccagca gctgcggctg gttttccagg   300
aatttcaaaa tatttctggg caagatatgg tagatgccat taatgaatgt tatgatggat   360
actttcagga gctgctggtt gcaattgttc tctgtgttcg agacaaacca gcctattttg   420
cttatagatt atatagtgca attcatgact ttggtttcca taataaaact gtaatcagga   480
ttctcattgc cagaagtgaa atagacctgc tgaccataag gaaacgatac aaagagcgat   540
atggaaaatc cctatttcat gatatcagaa attttgcttc agggcattat aagaaagcac   600
tgcttgccat ctgtgctggt gatgctgagg actactaaaa tgaagaggac ttggagtact   660
gtgcactcct ctttctagac acttccaaat agagattttc tcacaaattt gtactgttca   720
tggcactatt aacaaaacta tacaatcata ttttctcttc tatctttgaa attattctaa   780
gccaaagaaa actatgaatg aaagtatatg atactgaatt tgcctactat cctgaatttg   840
cctactatct aatcagcaat taaataaatt gtgcatgatg gaataataga aaaattgcat   900
tggaatagat tttatttaaa tgtgaaccat caacaaccta caacaag               947

<210> SEQ ID NO 16
<211> LENGTH: 1428
<212> TYPE: DNA
<213> ORGANISM: Homo sapiens

<400> SEQUENCE: 16
ttttcttgcc tgagtctgag gtgaacagtg aacatattta catttgattt aacagtgaac    60
cttaattctt tctggcttca cagtgaaaca agtttatgca atcgatcaaa tattttcatc   120
cctgaggtta acaattacca tcaaaatgtt ttgtggagac tatgtgcaag gaaccatctt   180
cccagctccc aatttcaatc ccataatgga tgcccaaatg ctaggaggag cactccaagg   240
atttgactgt gacaaagaca tgctgatcaa cattctgact cagcgctgca atgcacaaag   300
gatgatgatt gcagaggcat accagagcat gtatggccgg gacctgattg gggatatgag   360
ggagcagctt tcggatcact tcaaagatgt gatggctggc ctcatgtacc caccaccact   420
gtatgatgct catgagctct ggcatgccat gaagggagta ggcactgatg agaattgcct   480
cattgaaata ctagcttcaa gaacaaatgg agaaattttc cagatgcgag aagcctactg   540
cttgcaatac agcaataacc tccaagagga catttattca gagacctcag gacacttcag   600

```
agatactctc atgaacttgg tccaggggac cagagaggaa ggatatacag accctgcgat    660
ggctgctcag gatgcaatgg tcctatggga agcctgtcag cagaagacgg gggagcacaa    720
aaccatgctg caaatgatcc tgtgcaacaa gagctaccag cagctgcggc tggttttcca    780
ggaatttcaa atatttctg gcaagatat ggtagatgcc attaatgaat gttatgatgg       840
atactttcag gagctgctgg ttgcaattgt tctctgtgtt cgagacaaac cagcctattt    900
tgcttataga ttatatagtg caattcatga ctttggtttc cataataaaa ctgtaatcag    960
gattctcatt gccagaagtg aaatagacct gctgaccata aggaaacgat acaaagagcg    1020
atatggaaaa tccctatttc atgatatcag aaattttgct tcagggcatt ataagaaagc    1080
actgcttgcc atctgtgctg gtgatgctga ggactactaa aatgaagagg acttggagta    1140
ctgtgcactc ctctttctag acacttccaa atagagattt tctcacaaat ttgtactgtt    1200
catggcacta ttaacaaaac tatacaatca tattttctct tctatctttg aaattattct    1260
aagccaaaga aaactatgaa tgaaagtata tgatactgaa tttgcctact atcctgaatt    1320
tgcctactat ctaatcagca attaaataaa ttgtgcatga tggaataata gaaaaattgc    1380
attggaatag atttatttta aatgtgaacc atcaacaacc tacaacaa                 1428
```

<210> SEQ ID NO 17
<211> LENGTH: 324
<212> TYPE: PRT
<213> ORGANISM: Homo sapiens

<400> SEQUENCE: 17

```
Met Phe Cys Gly Asp Tyr Val Gln Gly Thr Ile Phe Pro Ala Pro Asn
1               5                   10                  15

Phe Asn Pro Ile Met Asp Ala Gln Met Leu Gly Gly Ala Leu Gln Gly
            20                  25                  30

Phe Asp Cys Asp Lys Asp Met Leu Ile Asn Ile Leu Thr Gln Arg Cys
        35                  40                  45

Asn Ala Gln Arg Met Met Ile Ala Glu Ala Tyr Gln Ser Met Tyr Gly
    50                  55                  60

Arg Asp Leu Ile Gly Asp Met Arg Glu Gln Leu Ser Asp His Phe Lys
65                  70                  75                  80

Asp Val Met Ala Gly Leu Met Tyr Pro Pro Leu Tyr Asp Ala His
                85                  90                  95

Glu Leu Trp His Ala Met Lys Gly Val Gly Thr Asp Glu Asn Cys Leu
            100                 105                 110

Ile Glu Ile Leu Ala Ser Arg Thr Asn Gly Glu Ile Phe Gln Met Arg
        115                 120                 125

Glu Ala Tyr Cys Leu Gln Tyr Ser Asn Asn Leu Gln Glu Asp Ile Tyr
    130                 135                 140

Ser Glu Thr Ser Gly His Phe Arg Asp Thr Leu Met Asn Leu Val Gln
145                 150                 155                 160

Gly Thr Arg Glu Glu Gly Tyr Thr Asp Pro Ala Met Ala Ala Gln Asp
                165                 170                 175

Ala Met Val Leu Trp Glu Ala Cys Gln Gln Lys Thr Gly Glu His Lys
            180                 185                 190

Thr Met Leu Gln Met Ile Leu Cys Asn Lys Ser Tyr Gln Gln Leu Arg
        195                 200                 205

Leu Val Phe Gln Glu Phe Gln Asn Ile Ser Gly Gln Asp Met Val Asp
    210                 215                 220
```

```
Ala Ile Asn Glu Cys Tyr Asp Gly Tyr Phe Gln Glu Leu Leu Val Ala
225                 230                 235                 240

Ile Val Leu Cys Val Arg Asp Lys Pro Ala Tyr Phe Ala Tyr Arg Leu
                245                 250                 255

Tyr Ser Ala Ile His Asp Phe Gly Phe His Asn Lys Thr Val Ile Arg
            260                 265                 270

Ile Leu Ile Ala Arg Ser Glu Ile Asp Leu Leu Thr Ile Arg Lys Arg
        275                 280                 285

Tyr Lys Glu Arg Tyr Gly Lys Ser Leu Phe His Asp Ile Arg Asn Phe
    290                 295                 300

Ala Ser Gly His Tyr Lys Lys Ala Leu Leu Ala Ile Cys Ala Gly Asp
305                 310                 315                 320

Ala Glu Asp Tyr
```